United States Patent [19]

Saville

[11] Patent Number: Plant 5,968

[45] Date of Patent: May 5, 1987

[54] ROSE PLANT NAMED SAVASON

[75] Inventor: F. Harmon Saville, Rowley, Mass.

[73] Assignee: Nor'East Miniature Roses, Inc., Rowley, Mass.

[21] Appl. No.: 775,039

[22] Filed: Sep. 11, 1985

[51] Int. Cl.[4] ..... A01H 5/00

[52] U.S. Cl. ..... Plt./10

[58] Field of Search ..... Plt./10

*Primary Examiner*—Robert E. Bagwill
*Attorney, Agent, or Firm*—Vincent G. Gioia

[57] ABSTRACT

A new miniature rose variety of currant red flower coloring which holds well upon aging.

1 Drawing Figure

1

The present invention relates to a new and distinct variety of rose plant of the miniature rose class, which was originated by my crossing as seed parent the rose known as "Sheri Ann" (U.S. Plant Pat. No. 3,826) and as pollen parent my seedling ("Yellow Jewel"×'-'Tamango"). The varietal denomination of this new variety is "Savason".

Among the novel characteristics possessed by this new variety which distinguish it from its parents and all other varieties of which I am aware are its flowers of unusually stable currant red coloring that maintain their color and form upon aging. Flowers are long lasting on the plant and are produced in large sprays. Asexual reproduction by budding of the new variety as performed in Essex County, Mass., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in color description herein refers to plate numbers in the aforementioned color chart, e.g., "46A" is plate 46A of The Royal Horticultural Society Colour Chart.

Parentage: Seedling.
- *Seed parent.*—"Sheri Ann".
- *Pollen parent.*—Unpatented seedling ("Yellow Jewel"×"Tamango").

Class: Miniature.

The following observations are made of specimens grown outdoors in Essex County, Mass., during the month of June.

FLOWER

Blooming habit: Continuous.

A. Bud:
- (1) *Size.*—Medium.
- (2) *Form.*—Ovate.
- (3) *Color.*—When sepals first divide — currant red near 46A to 46B. When petals begin to unfurl — color remains near 46A to 46B.
- (4) *Sepals.*—Longer than bud, lightly foliated.

2

- (5) *Peduncle.*—Length — about 1 to $1\frac{1}{4}$". Aspect — straight. Strength — erect. Color — near 144B.

B. Bloom:
- (1) *Size.*—Average size when fully expanded — about $1\frac{1}{4}$ to $1\frac{1}{2}$ inches.
- (2) *Borne.*—Many together in large sprays.
- (3) *Form.*—Cupped, becoming flat, outer petals reflex and roll under upon opening.
- (4) *Petalage.*—Number of petals under normal conditions — about 25 to 30.
- (5) *Color.*—After sepals fall, flower coloring remains relatively stable currant red, near 46A to 46B through opening stages. General tonality from a distance remains the same coloring.

C. Petals
- (1) *Texture.*—Thick.
- (2) *Appearance.*—Inside — very velvety. Outside — satiny.
- (3) *Form.*—Wedge shaped, apex pointed.
- (4) *Arrangement.*—Regularly arranged, imbricated.
- (5) *Petaloids in center.*—Few.
- (6) *Persistence.*—Drop off cleanly.
- (7) *Fragrance.*—Slight.
- (8) *Lasting quality.*—Very long lasting on plant.

REPRODUCTIVE ORGANS

A. Stamens, filaments and anthers:
- (1) *Arrangement.*—Regular arrangement around styles.
- (2) *Color.*—Near 21B.

B. Pollen:
- *Color.*—Near 26A.

C. Styles: Medium length.

D. Stigmas:
- *Color.*—Near 55D.

E. Hips: None observed.

PLANT

A. Form: Upright.

B. Growth: Very vigorous.
- *Height attained.*—About 16 to 18 inches.

C. Foliage: Compound 5 to 7 leaflets.
- (1) *Size.*—Medium.
- (2) *Quantity.*—Abundant.
- (3) *Color.*—New foliage: Upper side — near to 137B. Under side — near to 138B. Old foliage: Upper side — near 137B. Under side — near 138B.
- (4) *Shape.*—Oval, pointed.

(5) *Texture.*—Upper side is semi-glossy and under side is matte.

(6) *Edge.*—Serrated.

(7) *Serration.*—Serrate.

(8) *Leaf stem.*—Color — near 147B. Under side — near 146B.

(9) *Stipules.*—Medium, slightly bearded.

(10) *Resistance to disease.*—Blackspot — average. Mildew — average. Rust — average.

D. Wood:

(1) *New wood.*—Color — near 146B. Bark — smooth.

(2) *Old wood.*—Color — near 143A. Bark — semi-smooth.

E. Thorns:

(1) Thorns.—Quantity (main stalk — ordinary. On laterals from stalk — few. Form — heavy base, straight, pointed slightly downward. Length — medium. Color — near 180D. Position — irregular.

(2) *prickles.*—None.

F. Winter hardiness: Requires ordinary protection in extreme climates.

I claim:

1. A new and distinct variety of rose plant of the miniature rose class, substantially as shown and described, characterized particularly by flowers of unusually stable currant red coloring that hold color well upon aging.

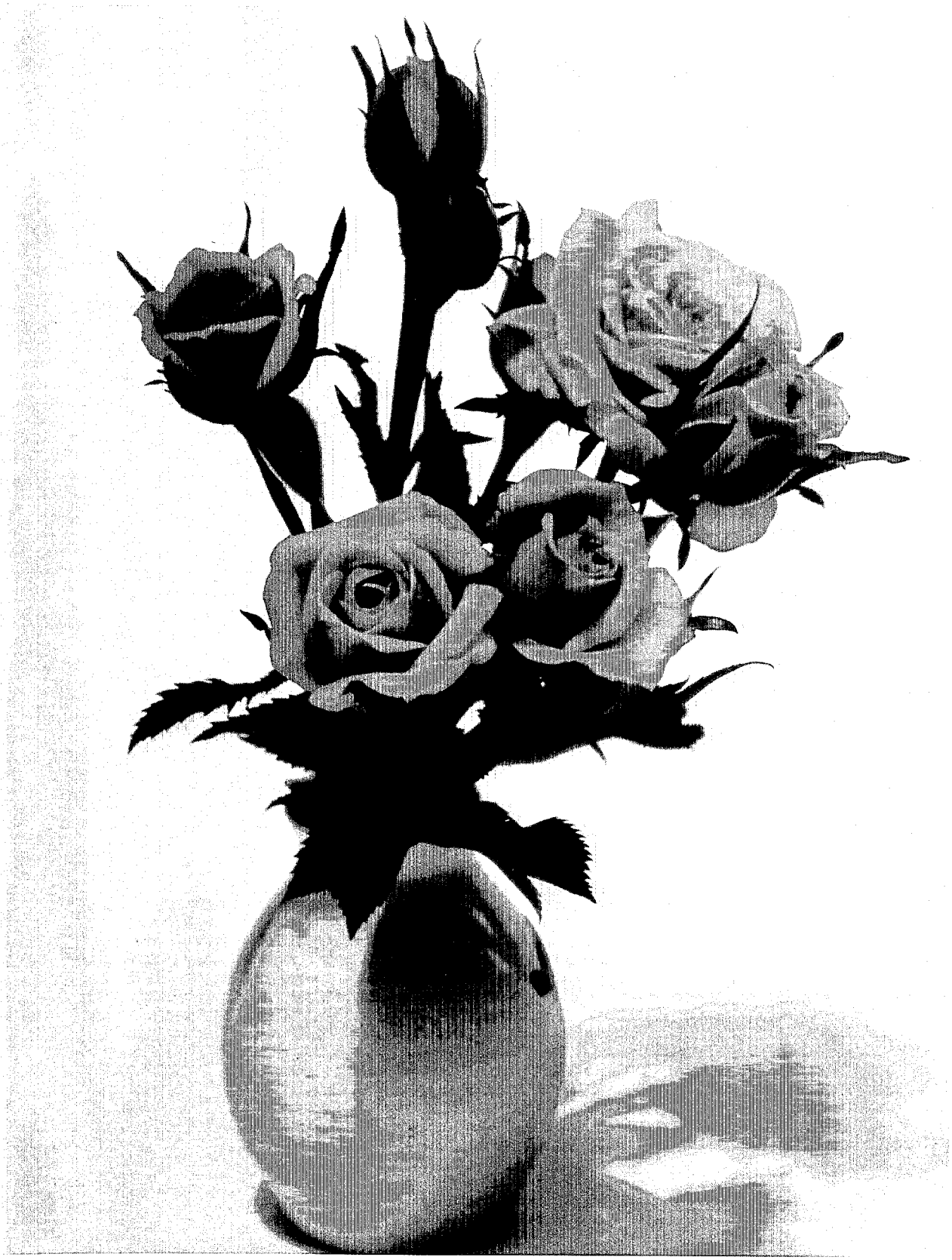

* * * * *